(12) United States Patent
Montgomery

(10) Patent No.: US 6,472,453 B2
(45) Date of Patent: Oct. 29, 2002

(54) COMPOSITIONS FOR MAKING AN ARTIFICIAL PROSTHESIS

(75) Inventor: R. Eric Montgomery, Monterey, MA (US)

(73) Assignee: Applied Dental Sciences, Inc., Lee, MA (US)

( * ) Notice: Subject to any disclaimer, the term of this patent is extended or adjusted under 35 U.S.C. 154(b) by 0 days.

(21) Appl. No.: 10/033,077

(22) Filed: Nov. 1, 2001

(65) Prior Publication Data

US 2002/0086915 A1 Jul. 4, 2002

Related U.S. Application Data

(63) Continuation of application No. 09/208,969, filed on Dec. 10, 1998, now Pat. No. 6,348,518.
(60) Provisional application No. 60/069,021, filed on Dec. 10, 1997.

(51) Int. Cl.$^7$ ................................................. A61K 6/10
(52) U.S. Cl. ........................................ 523/109; 525/300
(58) Field of Search ............................ 523/109; 525/300

(56) References Cited

U.S. PATENT DOCUMENTS

| | | |
|---|---|---|
| 3,657,117 A | 4/1972 | Pfitzner et al. ............... 210/31 |
| 4,495,172 A | 1/1985 | Orlowski et al. |
| 4,871,534 A | 10/1989 | Montgomery |
| 5,770,184 A | 6/1998 | Keller |
| 5,830,442 A | 11/1998 | Beaver |

OTHER PUBLICATIONS

Dialogue Computer Search Results, No date.

*Primary Examiner*—Paul R. Michl
(74) *Attorney, Agent, or Firm*—Banner & Witcoff, Ltd.

(57) ABSTRACT

Novel compositions and methods are disclosed for manufacturing an artificial prosthesis, whether for medical, dental or cosmetic use. The compositions include a family of monomeric esters having increased solvency and decreased volatility.

42 Claims, No Drawings

COMPOSITIONS FOR MAKING AN ARTIFICIAL PROSTHESIS

RELATED APPLICATIONS

This application is a continuation of U.S. application Ser. No. 09/208,969, filed on Dec. 10, 1998; 6,348,518, which claims the benefit of U.S. Provisional Application No. 60/069,021, filed Dec. 10, 1997.

BACKGROUND OF THE INVENTION

1. Field of the Invention

Embodiments of the present invention relate in general to compositions and methods useful in the preparation of an artificial prothesis, whether for medical, dental or cosmetic use. Embodiments of the present invention are more particularly directed to compositions which include ester compounds having high solvency and low volatility.

2. Description of Related Art

Materials science has provided a plethora of compositions that can be transformed from an initial, malleable state to a final, non-malleable state, generally through the process of heating, the application of pressure, and/or the inducement of polymerization. Such compositions may be first molded into a desired shape, then subsequently induced to transform into a final, non-deformable shape identical (or nearly so) to the original molded shape. Such processes may employ heat or pressure (or both) to transform materials into a desired shape by manipulation of the physical properties of the material itself, or may alternatively utilize initiators and/or activators to begin a polymerization reaction throughout the shaped mass.

The class of materials known as acrylics (which, for the purpose of this disclosure, shall mean compositions comprised wholly or in part of acrylate and/or methacrylate monomers and/or polymers, alone or in combination with each other and/or other unsaturated and/or saturated compounds) has gained acceptance as being particularly suited for the formation of prosthetics to be placed into contact with the body. In particular, acrylics have been used to form dental restorative materials, dentures, temporary crown and bridge materials, and artificial fingernails and toenails, as well as having been employed as adhesion promoters at the interface between a biological surface (herein defined as any external or internal surface of a living organism) and a prosthetic (in order to provide the extended wear time required of, for instance, a permanent dental restorative material). Curable acrylic compositions, when properly initiated or catalyzed, undergo free-radical addition reaction polymerization, which is exothermic (generates heats) in character.

A large number of acrylic compositions, such as those finding utility as artificial fingernails and dentures, are formulated in separate phases or parts, one or both of the parts containing an element required for polymerization to occur. It is not until the parts are combined that the composition can undergo a polymerization reaction, and the concentration of the polymerization-inducing elements (for instance a free-radical polymerization initiator and a free-radical polymerization promoter) in each part can determine the rate and extent of polymerization for the entire composition. It is often required that the input of heat or light energy is required after combining all of the composition components in order to effect polymerization.

An example of a multi-component composition includes at least one liquid phase and one solid phase, said phases being combined in a specified ratio just prior to being shaped into, for instance, a prosthetic device or object. Upon combining the liquid and solid phases, and, optionally, exposing the resulting mixture to heat and/or light energy, a free-radical polymerization process is induced and proceeds at a rate relative to the concentration of polymerization initiators and/or promoters contained therein. A light-induced polymerization reaction is initiated by exposing the composition to a particular spectrum of light that overlaps that of a photoinitiator contained in the composition.

A particularly intractable problem presented by currently available multi-component compositions comprising a liquid acrylic monomer and a solid polymer stems from the correlation between a liquid acrylic monomer's solvating capabilities and its volatility. While many liquid acrylic monomers possess the ability to quickly absorb and dissolve the solid polymers intended to be used with them to form a prosthesis or other solid object, these same monomers seem to be highly volatile and have objectionable and possibly unhealthy odors. Most monomers with low volatility, such as the C4 and higher methacrylate monomers, tend to lack the solvency characteristics required to adequately dissolve the solid polymer phase of the composition. It has been reported that insufficient salvation of the solid polymer phase results in a finished cured polymer that lacks desirable physical properties, such as high tensile and flexural strength.

On the other hand, monomers with the required solvency characteristics tend to have high volatilities. The most frequently employed monomer for making dentures, methyl methacrylate, is easily detected by smell in a large room containing but a small volume of liquid. Similarly, ethyl methacrylate, the most commonly employed artificial fingernail liquid monomer, is a bane to nail salons due to its characteristic odor that is detectable at extremely low levels in air (methyl methylacrylate can be detected by humans at a concentration of as little as 750 parts per billion in standing air while ethylmethacrylate can be detected by humans at a concentration of as little as 170 parts per billion in standing air).

There have been attempts to provide alternative liquid monomers for the applications described above. Monomers such as methoxyethyl methacrylate, methoxyethoxyethyl methacrylate, ethoxyethoxyethyl methacrylate, tetrahydrofurfuryl methacrylate, and hydroxyethyl methacrylate have been employed alone or in combination with other monomers in an attempt to provide odorless or low-odor liquid acrylic monomers for multi-component acrylic systems. Methoxyethyl methacrylate is manufactured from methoxyethanol and thus contains it as a toxic impurity. Methoxyethoxyethyl and ethoxyethoxyethyl methacrylate have a better safety profile, but suffer from a relatively low solvating ability compared to liquid acrylic monomers such as methyl and ethyl methacrylate. Tetrahydroturfuryl methacrylate possesses a distinct and objectionable odor, and is also limited in its solvating ability. Hydroxyethyl methacrylate, in addition to having limited solvating capabilities, is highly hygroscopic in its polymerized form; its water absorption properties can render polymers containing it highly susceptible to physical degradation from hydrolysis.

A need therefore existst to develop compositions including an acrylic monomer which are useful in forming a polymerized prosthesis while avoiding the problems associated with prior art compositions using highly volatile acrylic monomer compounds. A further need exists to provide an acrylic monomer having a high degree of solvency and a low level of odor for use in a multi-component composition that combines a liquid component and a solid component prior to desired use.

BRIEF SUMMARY OF THE INVENTION

Embodiments of the present invention are directed to compositions useful in making an artificial prosthesis, including a medical, dental or cosmetic prosthesis. Embodiments of the present invention are further advantageously directed to methods using monomeric ester compounds capable of polymerization and having low volatility or low or no odor and/or desirable solvation properties with respect to acrylate or methacrylate based polymers in the manufacture of an artificial prosthesis. According to one embodiment of the present invention, a composition is provided which includes one or more of a polymeric compound, a polymerization catalyst, a polymerization promoter, a solvent and a compound of formula I below:

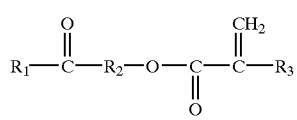

Formula I wherein $R_1$ is hydrogen or $C_1$–$C_{10}$ straight or branched chain, substituted or unsubstituted, saturated or unsaturated alkyl, $R_2$ is $C_1$–$C_{10}$ straight or branched chain, substituted or unsubstituted, saturated or unsaturated alkyl, $R_3$ is hydrogen or $C_1$–$C_{10}$ straight or branched chain, substituted or unsubstituted, saturated or unsaturated alkyl. The monomer compounds of Formula I advantageously exhibit desirable solvency and low volatility properties in a composition compared to prior art monomer compounds, such as methyl or ethyl methacrylate monomer compounds, thereby advantageously providing a reduction of evaporation and loss of the monomer during the prosthesis-forming process. The advantageous low volatility of the monomer compounds of Formula I is chiefly observed by the absence of odor or presence of a low amount of odor during the prosthesis-forming process, as compared to the very unpleasant and/or unhealthy odor present when using monomer compounds such as methyl or ethyl methacrylate monomers. The volatility of the compounds of formula I may also be measured by methods well known in the art and demonstrated to have a significantly lower volatility than known monomer compounds such as methyl or ethyl methacrylate monomers.

The low volatility of the monomer of Formula I, therefore, also advantageously reduces unnecessary and possibly unhealthy inhalation of the monomer in the workplace, while advantageously producing a composition suitable for forming a hardened artificial prosthesis, such as a denture or an artificial fingernail. The ester portion of the compound, i.e. that bound to the free oxygen of the carboxylic acid group, advantageously contributes to good solvent characteristics with respect to acrylate or methacrylate based polymers in the compositions of the invention while reducing the overall volatility of the compounds as compared to known monomers such as methyl and ethyl methacrylate monomers without rendering useless the ability of the monomer to polymerize or otherwise solvate an acrylate or methacrylate based polymer. The R groups of formula I advantageously decrease the volatility of the compounds over prior art methyl and ethyl methacrylates by increasing the molecular weight of the compound. The advantage of good solvency in dental and cosmetic products becomes apparent, especially in the denture and artificial fingernail art, where the flow properties of the composition after mixing of liquid monomeric compounds with solid polymeric acrylate or methacrylate compounds are essential to the handling, shaping, or sculpting of the resulting composition prior to hardening. In addition, the compounds of formula I may be formulated to be relatively insoluble in water, thereby avoiding prior art problems of degradation due to hydrolysis.

The above components may be combined stepwise or all at once to form a composition. Alternatively, a liquid formulation may be formed by combination of the compound of formula I which may act as both monomer and solvent, and an additional solvent if desired with or without the polymerization promoter which may then be contacted with a powder formulation including the polymeric compound and the polymerization catalyst. The polymeric compound is used as a filler compound to impart desirable characteristics to the composition before, during and after curing. Additional components such as comonomers, copolymers, photoinitiators, polymerization accelerators, UV light absorbers, polymerization inhibitors, pigments, antioxidants, hardeners, plasticizers, opacifiers, colorant extenders or dispersing agents may also be added to the compositions of the present invention. The composition resulting from the combination of the liquid formulation and the powder formulation then is allowed or otherwise induced by, for example, heat or light to polymerize into a solid structure after a sufficient period of time.

Accordingly, it is an object of the present invention to provide a composition which is useful in the manufacture of an artificial prosthesis, whether medical, dental or cosmetic. It is a further object of the present invention to provide a composition and method which includes a monomeric ester species having a low volatility or low or no odor and a good solvency, thereby avoiding the prior art problems of loss of monomer due to evaporation or unhealthy inhalation of volatile monomer species. It is a further object of the present invention to provide a medical, dental or cosmetic prosthesis manufactured using the monomer compounds of formula I.

Other objects, features and advantages of certain embodiments of the present invention will become more fully apparent from the following description taken in conjunction with the accompanying claims.

DETAILED DESCRIPTION OF CERTAIN PREFERRED EMBODIMENTS

The principles of the present invention may be applied with particular advantage to obtain compositions and methods for the preparation of an artificial prosthesis including a medical, dental or cosmetic prosthesis.

The present invention, in one embodiment, is directed to a composition that polymerizes into a prosthesis, i.e. a hardened form of desired shape. The composition may be provided as a multi-component formulation including one or more of a polymeric compound, a polymerization catalyst, a polymerization promoter or accelerator, a solvent and a compound of formula I below:

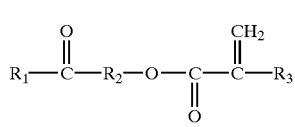

Formula I wherein $R_1$ is hydrogen or $C_1$–$C_{10}$ straight or branched chain, substituted or unsubstituted, saturated or unsaturated alkyl, $R_2$ is $C_1$–$C_{10}$ straight or branched chain, substituted or unsubstituted, saturated or unsaturated alkyl, $R_3$ is hydrogen or $C_1$–$C_{10}$ straight or branched chain, substituted or unsubstituted, saturated or unsaturated alky. According to an additional embodiment, $R_1$ is $C_1$–$C_{10}$ straight or branched chain, substituted or unsubstituted, saturated or unsaturated alkyl, $R_2$ is $C_1$–$C_5$ straight or branched chain, substituted or unsubstituted, saturated or unsaturated alkyl, $R_3$ is hydrogen or $C_1$–$C_5$ straight or branched chain, substituted or unsubstituted, saturated or unsaturated alkyl. According to a further additional embodiment of the present invention, $R_1$ is $C_1$–$C_5$ straight chain alky, $R_2$ is $C_1$–$C_5$ straight chain alkyl, and $R_3$ is hydrogen or methyl.

The monomer compounds of formula I are advantageously employed to not only prepare an artificial prosthesis, but also to reduce loss of monomer during the mixing and fabrication process as a result of evaporation and also to reduce noxious fumes or odors which may present unhealthy working conditions. These advantageous aspects of the present invention are attributable to the desirable solvency and low volatility of the compounds of Formula I.

According to one embodiment, the components of the composition may be mixed together simultaneously or added sequentially in a manner to promote the polymerization of the resulting composition. The extent that components may be added together simultaneously or sequentially depends on the rate of polymerization of the resulting composition, i.e. the rate of polymerization should be slow enough to allow for the composition to be fabricated into a desired shape prior to hardening. The rate of polymerization is determined in one aspect by the amounts and activity of catalysts, initiators, activators, and/or accelerators which may be employed, as well as whether the polymerization is chemically induced or induced by heat or light.

In order to prevent premature polymerization of the monomer compounds of formula I, a two component system is provided. A liquid component including the monomer compound of formula I, a solvent (which may be the same or different from the monomer compound of formula I) and optionally, a polymerization promoter or accelerator is prepared. A powder component including the polymeric compound and a polymerization catalyst is then prepared. The liquid component and the powder component can then be contacted together to form a slurry composition which may then be applied, shaped, sculpted or molded into a desired shape shortly before the desired polymerization. Other techniques used to mix and polymerize components of the type disclosed above is disclosed in *Encyclopedia of Polymer Science and Technology*, John Wiley and Sons, Inc., vol. 1, pp 263–297 (1964) hereby incorporated by reference in its entirety.

The compounds of formula I may be prepared according to methods well known in the art of organic chemistry including those disclosed in U.S. Pat. No. 3,657,117 hereby incorporated by reference in its entirety. The low volatility of the compounds of formula I as compared to prior art monomers, such as methyl and ethyl methacrylate, is chiefly observed in the substantially reduced odor associated with the compounds of formula I. Standard well known techniques may be employed to confirm the reduced volatility of the compounds as compared to prior art monomers, such as methyl and ethyl methacrylate. While not wishing to be bound by any scientific theory, the ester portion of the compounds of formula I is believed to impart desirable solvency properties with respect to ester-based polymeric compounds, such as polyacrylates or polymethacrylates, and is further believed to lower the volatility of the compound as compared to methyl and ethyl methacrylates due to the increased molecular weight of the compound.

The compounds of formula I are present in the liquid component of the two component system in an amount between 10% to 90% by weight of the liquid component or the composition and more particularly in an amount between 50% to 85%, and preferably between 75% to 85% by weight and more preferably about 80% by weight of the liquid component or the composition. It is to be understood that the compounds of formula I may be present in any amount suitable to produce a polymerized prosthesis and that one of skill in the art will be able to determine appropriate amounts of the compounds of formula I, as well as, other components in the inventive compositions as a whole based upon the disclosure and examples provided herein.

In addition to the compounds of formula I, the inventive compositions may contain one or more co-monomers, typically used to adjust the final physical properties of the polymerized prosthetic or object. The comonomers employed should not significantly alter the high solvency and low odor properties of the liquid component. Examples of comonomers include di- and tri-functional acrylic monomers that may be utilized as polymerization crosslinkers in the range of from about 0.10% by weight of the liquid component to about 20% by weight of the liquid component. Such crosslinking comonomers include ethylene glycol dimethacrylate, diethylene glycol dimethacrylate, triethylene glycol dimethacrylate, trimethyolpropane trimethacrylate, 1,4-butanediol dimethacrylate, 1,6-hexanediol dimethacrylate, 1,1 2-dodecanediol dimethacrylate, polyethylene glycol dimethacrylate, 2,2-bis [4'-(3"-methacryloyl-2"-hydroxypropoxy)phenyl]propane (bis-GMA), ethoxylated bisphenol A dimethacrylate, urethane dimethacrylate, and others. Other comonomers include monofunctional, low odor methacrylates such as hydroxyethyl methacrylate and hydroxypropyl methacrylate.

A solid polymeric compound used as a filler portion is included in the composition to provide bulk, tensile strength, and to control flow properties of the liquid-solid component mixture from (1) the point in time at which the components are first contacted or admixed to (2) the point in time when the beginning of polymerization occurs. The polymeric filler controls the above properties through a combination of one or more of the following attributes: polymer composition, i.e., the chemical nature of the polymer backbone, particle size distribution of the polymeric filler, i.e., the physical size of the individual polymer particles, and the molecular weight of the polymer. The solid polymeric filler may be included in the composition in an amount from about 10% by weight to about 90% by weight of the composition as a whole, particularly 25% to 75%, and preferably 40% to 60% depending on the desired flow properties and the particular application in which it is employed. Suitable solid polymeric fillers include polymers and copolymers of the poly lower alkyl methacrylate or acrylic ester polymers such as $C_1$ to $C_5$ straight or branched lower alkylmethacrylate polymers, including poly(methyl methacrylate), poly(ethyl methacrylate), poly(butyl methacrylate), poly(isobutyl methacrylate), poly(ethyl-co-methyl methacrylate), poly (methyl-co-butyl methacrylate), poly(methyl-co-ethyl-co-butyl methacrylate), poly(ethyl-co-butyl methacrylate) and combinations thereof In addition, polymers and copolymers of lower alkyl methacrylates can be prepared and utilized that contain acrylic or methacrylic acid as a comonomer in the polymer chain. The acid functionality of such polymer fillers is seen to increase the hardness and adhesion of the inventive compositions, desirable traits in certain applications.

Suitable polymerization initiators or catalysts useful in the present invention include peroxides which cause the composition to cure in situ once all of the necessary components are contacted together. Examples of suitable initiators or catalysts include lauroyl peroxide, benzoyl peroxide, 5-butyl barbituric acid, 1-benzyl-5-phenyl barbituric acid, other 5-alkyl or 5-aryl barbituric acid compounds and the like. Initiators or catalysts of the present invention are present in an amount between about 0.1% to about 5.0% by weight of the solid component or the composition as a whole.

The ability of the polymerization catalyst to cure the compositions of the present invention may be enhanced through the optional use of an accelerator or polymerization promoter which may be included as part of the liquid component identified above. Suitable accelerators or polymerization promoters include the family of tertiary aromatic amines such as those disclosed in U.S. Pat. No. 4,495,172 hereby incorporated by reference in its entirety. Specific polymerization promoters include N,N-dimethyl-p-toluidine, N,N-diethyl-p-toluidine and N,N-bis(2-hydroxyethyl-p-toluidine, dimethylaminoethyl methacrylate, ethyl-para-dimethylaminoethyl benzoate, dihydroxyethyl-para-toluidine and the like. Accelerators or polymerization promoters of the present invention are present in an amount between about 0.1% to about 7.0% by weight of the liquid component or the composition as a whole.

The compositions may additionally contain one or more photoinitiators in order to render the composition's combined liquid and solid components sensitive to light, thereby effecting polymerization by actinic energy at a wavelength or wavelengths corresponding to the spectrum of said photoinitiators. Examples of useful photoinitiators include camphorquinone, benzil, 2-hydroxy-2-methyl-1-phenyl-propane-1-one (Darocure 1173, EM Chemicals, Hawthorne, N.Y.), and 1-hydroxycyclohexyl phenyl ketone (Irgacure 184, Ciba-Geigy Corporation, Hawthorne, N.Y.). The above photoinitiators may be included in the composition at a level of from about 0.1% by weight to about 4.0% by weight of the composition as whole.

The composition may also contain one or more compounds containing a hydroxyl moiety, such as isopropyl alcohol, hydroxyethyl methacrylate, and hydroxypropyl methacrylate, in order to accelerate the polymerization process once it has been initiated. Such compounds may be included at a level of from about 0.1% by weight to about 10% by weight of the composition as a whole.

In order to prevent polymer degradation and yellowing from UV light after the polymerization process has been completed, a UV light absorber may be included in the composition at a level from about 0.1% by weight to about 3.0 percent by weight of the composition as a whole. Examples of suitable UV light absorbers found to have utility in the present inventive compositions are 2(2'-hydroxy-5'-methyl phenyl)benzotriazole (Tinuvin P, Ciba-Geigy Corporation, Hawthorne, N.Y.), 2-hydroxy4-methoxybenzophenone and 2-cyano-3,3'-diphenylacrylic acid 2'-ethylhexyl ester (Uvinul M40 and Uvinul N539, respectively, BASF, Ludwigshafen, Germany).

In order to further control the rate of polymerization and to provide stability to the liquid monomer component of the composition, a polymerization inhibitor such as the methyl ether of hydroquinone (MEHQ) and/or 3-butyl-4-hydroxy toluene (BHT) is seen to have particular utility. The concentration of polymerization inhibitor included in the composition as a whole can be from about 10 parts per million (0.001%) to about 5000 parts per million (1.0%). Lower levels of polymerization inhibitor are preferred due their deleterious effect at high concentrations on the color stability of the resulting polymerized composition.

The inventive compositions may also contain from about 0.5% to about 5.0% of a pigment or dye, in order to adjust the color of the resulting polymerized composition. For example, a red lake pigment and titanium dioxide are added to a denture base polymer composition in order to provide pigmentation that closely matches that of the oral mucosa. Suitable pigments and dyes include, but are not limited to, titanium dioxide, zinc oxide, insoluble lakes, and soluble dyes. Pigments based on, for instance, barium may be added in order to make the resulting polymerized composition radiopaque to x-rays.

The following examples are set forth as representative of the present invention. These examples are not to be construed as limiting the scope of the invention as these and other equivalent embodiments will be apparent in view of the present disclosure, tables and accompanying claims.

EXAMPLE I

In order to determine the ability of the inventive compositions to produce an artificial prosthesis, an artificial fingernail formed from one embodiment of the inventive compositions was prepared as follows. A liquid component A and a solid component B were prepared having the ingredients identified below.

| Ingredient | Amount |
| --- | --- |
| Part A | |
| Acetoxyethyl methacrylate | 80.00 grams |
| Triethylene glycol dimethacrylate | 10.00 grams |
| Dimethyl-p-toluidine | 1.00 grams |
| TOTAL | 100.00 grams |
| Part B | |
| Polyethylmethacrylate | 99.30 grams |
| Benzoyl peroxide | 0.70 grams |
| TOTAL | 100.00 grams |

In order to create an artificial fingernail, an artist's brush is dipped into a reservoir containing a small amount of the liquid component of Part A. After the brush bristles have wetted out, the brush is contacted with a separate reservoir containing the powder component of Part B, allowing the powder particles to absorb into the liquid on the brush. The resultant slurry is retained on the brush and has the consistency similar to wet snow—it is easily moved around the natural fingernail surface in order to shape an artificial fingernail, yet does not "slump" once shaped as desired.

The inventive composition of Example I is seen to polymerize into a fused mass in approximately 4 minutes at room temperature and has good tensile strength and clarity-properties desirable in an artificial fingernail composition. The most notable advantage is the lack of noticeable odor when being applied—a significant improvement over prior art compositions containing high volatility monomeric methacrylates such as ethyl and butyl methacrylate.

EXAMPLE II

A denture base composition was prepared that utilized acetoxyethyl methacrylate as the liquid monomeric component and poly(ethyl methacryate) as the solid polymeric component. The liquid contained 4% by weight of 1,6-hexanediol dimethacrylate as a crosslinking comonomer. The polymer contained approximately 0.6% by weight benzoyl peroxide in order to initiate the polymerization reaction upon heating the admixed composition. A mix ratio of 2 parts solid polymer to 1 part liquid monomer (by weight) was used.

Upon mixing the liquid and solid components described above, the initial slurry gradually became doughlike in consistency, at which point it was placed into the cavity of a dental flask that normally houses the prosthetic teeth. The flask was sealed and placed into a water bath at approximately 75° C. for a period of 8 hours. After this time, the flask was removed and cooled for 1 hour at room temperature, and subsequently immersed in cool water for another 30 minutes. The flask was opened and the polymerized material was examined for voids and imperfections.

The polymerized composition prepared above was hard and transparent, and appeared to be highly suitable as a denture material. The polymer was resistant to surface softening with 190 proof ethanol.

EXAMPLE III

The following two-component photopolymerizable orthodontic adhesive for attaching braces and other type devices to teeth was prepared.

| Ingredient | Amount |
| --- | --- |
| Part A | |
| Acetoxyethyl methacrylate | 76.50 grams |
| Hydroxyethyl methacrylate | 18.00 grams |
| Methacryloyloxyethyl maleate | 5.00 grams |
| Camphorquinone | 0.50 grams |
| TOTAL | 100.00 grams |
| Part B | |
| Poly(ethyl-co-methyl methacrylate) | 99.00 grams |
| Ethyl-para-dimethylaminoethyl benzoate | 1.00 grams |
| TOTAL | 100.00 grams |

Part A was combined with Part B at a weight ratio of approximately 1 to 1 and mixed thoroughly for a period of five minutes. The resulting paste was used to adhere a metal bracket onto an extracted human tooth by brushing the admixed composition onto the facing surface of the metal bracket, then placing the metal bracket in contact with the tooth. Light energy from an Optilux 500 dental curing light (Demetron Corporation, Danbury, Conn.) was used to polymerize the adhesive over an exposure time of approximately 5 minutes. The metal bracket was thereby securely fastened to the tooth surface.

EXAMPLE IV

A single component light-cured fingernail composition was prepared utilizing acetoxyethyl methacrylate as a diluent and poly(methyl methacrylate) as a filler.

| | |
| --- | --- |
| Acetoxyethyl methacrylate | 30.00 grams |
| Hydroxyethyl methacrylate | 5.00 |
| Ethylene glycol dimethacrylate | 12.00 grams |

| -continued | |
| --- | --- |
| 2-hydroxy-2-methyl-1-phenyl-propane-1-one | 1.00 grams |
| Poly(methyl methacrylate) | 52.00 grams |
| TOTAL | 100.00 grams |

The above composition was a dough-like material that could be shaped into an artificial fingernail or other similar prosthetic device. It was polymerized with an ultraviolet fluorescent lamp to a hard, fused polymer that was resistant to surface softening with acetone (commonly used in nail polish remover).

EXAMPLE V

Comparative Volatility Study

A comparative evaporation study was performed in order to determine the relative volatilities of several monomeric methacrylates. The percent weight loss of a 5.000 gram sample was determined over exactly 10 minutes by taring the sample on an analytical balance accurate to 0.00001 grams.

| Monomer | % Weight Loss |
| --- | --- |
| Methyl methacrylate (MMA) | 0.570% |
| Ethyl methacrylate (EMA) | 0.227% |
| Methoxyethoxyethyl methacrylate (MOEOEMA) | 0.066% |
| Hydroxyethyl methacrylate (HEMA) | 0.070% (Weight gain) |
| Acetoxyethyl methacrylate (AEMA) | 0.150% |

The weight gain demonstrated by the hydroxyethyl methacrylate was not unexpected due to the hygroscopic nature of this monomer. The low odor monomers tested, i.e. HEMA, MOEOEMA (which is disclosed in U.S. Pat. No. 4,871,534 hereby incorporated by reference in its entirety), and AEMA showed significantly lower evaporative volatility than their high odor methacrylate counterparts (MMA and EMA).

Comparative Solvating Study

Several methacrylate monomers were compared for their ability to dissolve a low molecular weight poly(ethyl methacrylate). A timer was started when 10 grams of the polymer was added to 100 grams of monomer while mixing with a magnetic stirring bar. Complete solution was considered complete upon attainment of clarity and the time recorded at this point.

| Monomer | Time to Solution |
| --- | --- |
| Ethyl methacrylate (EMA) | 180 seconds |
| Hydroxyethyl methacrylate (HEMA) | 1200 seconds |
| Methoxyethoxyethyl methacrylate (MOEOEMA) | 820 seconds |
| Acetoxyethyl methacrylate (AEMA) | 480 seconds |

The solvating ability of AEMA, while not as high as the EMA, is superior to all of the other low odor monomers tested.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention.

What is claimed is:

1. A composition capable of polymerizing into a solid form comprising:
    a polymeric filler compound in powder form;
    a polymerization catalyst; and
    a compound of the formula I

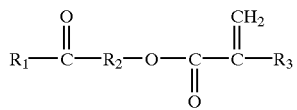

wherein $R_1$ is hydrogen or $C_1$–$C_{10}$ straight or branched chain, substituted or unsubstituted, saturated or unsaturated alkyl, $R_2$ is $C_1$–$C_{10}$ straight or branched chain, substituted or unsubstituted, saturated or unsaturated alkyl, and $R_3$ is hydrogen or $C_1$–$C_{10}$ straight or branched chain, substituted or unsubstituted, saturated or unsaturated alkyl.

2. The composition of claim 1 wherein $R_1$ is $C_1$–$C_5$ straight or branched chain, substituted or unsubstituted, saturated or unsaturated alkyl, $R_2$ is $C_1$–$C_5$ straight or branched chain, substituted or unsubstituted, saturated or unsaturated alkyl, $R_3$ is hydrogen or $C_1$–$C_5$ straight or branched chain, substituted or unsubstituted, saturated or unsaturated alkyl.

3. The composition of claim 1 wherein $R_1$ is $C_1$–$C_5$ straight chain alkyl, $R_2$ is $C_1$–$C_5$ straight chain alkyl, and $R_3$ is hydrogen or methyl.

4. The composition of claim 1 wherein the polymeric compound is present in an amount between 10% to 90% by weight of the composition.

5. The composition of claim 1 wherein the polymeric compound is an alkyl methacrylate or acrylate polymer.

6. The composition of claim 5 wherein the polymeric compound is selected from the group consisting of poly(methyl methacrylate), poly(ethyl methacrylate), poly(butyl methacrylate), poly(isobutyl methacrylate), poly(ethyl-co-methyl methacrylate), poly(methyl-co-butyl methacrylate), poly(methyl-co-ethyl-co-butyl methacrylate), and poly(ethyl-co-butyl methacrylate).

7. The composition of claim 1 wherein the polymerization catalyst is present in an amount between 0.1% to 5.0% by weight of the composition.

8. The composition of claim 1 wherein the polymerization catalyst is selected from the group consisting of benzoyl peroxide, peroxide, lauroyl peroxide, 5-alkyl barbituric acid, 5-aryl barbituric acid and 1-benzyl-5-phenyl barbituric acid.

9. The composition of claim 1 further including a polymerization promoter present in an amount between 0.1% and 7.0% by weight of the composition.

10. The composition of claim 1 wherein the polymerization promoter is a tertiary aromatic amine.

11. The composition of claim 10 wherein the promoter is selected from the group consisting of N,N-dimethyl-p-toluidine, N,N-diethyl-p-toluidine, N,N-bis(2-hydroxyethyl-p-toluidine, dimethylaminoethyl methacrylate, ethyl-para-dimethylaminoethyl benzoate, and dihydroxyethyl-para-toluidine.

12. The composition of claim 1 further comprising a comonomer or crosslinker present in an amount between 0.1% and 20% by weight of the composition.

13. The composition of claim 1 wherein the comonomer or crosslinker is selected from the group consisting of ethylene glycol dimethacrylate, diethylene glycol dimethacrylate, triethylene glycol dimethacrylate, trimethylolpropane trimethacrylate, 1,4-butanediol dimethacrylate, 1,6-hexanediol dimethacrylate, 1,12-dodecanediol dimethacrylate, polyethylene glycol dimethacrylate, 2,2-bis[4'-(3"-methacryloyl-2"-hydroxypropoxy)phenyl]propane (bis-GMA), ethoxylated bisphenol A dimethacrylate, urethane dimethacrylate, hydroxyethyl methacrylate and hydroxypropyl methacrylate.

14. The composition of claim 1 further comprising a photoinitiator present in an amount between 0.1% to 0.4% by weight of the composition.

15. The composition of claim 14 wherein the photoinitiator is selected from the group consisting of camphorquinone, benzil, 2-hydroxy-2-methyl-1-phenyl-propane-1-one and 1-hydroxycyclohexyl phenyl ketone.

16. The composition of claim 1 further comprising a UV light absorber present in an amount between 0.1% to 3.0% by weight of the composition.

17. The composition of claim 16 wherein the UV light absorber is selected from the group consisting of 2(2'-hydroxy-5'-methyl phenyl)benzotriazole, 2-hydroxy-4-methoxybenzophenone and 2-cyano-3,3'-diphenylacrylic acid 2'-ethylhexyl ester.

18. The composition of claim 1 further comprising a polymerization inhibitor present in an amount between 10 ppm to 5000 ppm.

19. The composition of claim 18 wherein the polymerization inhibitor is a methyl ether of hydroquinone or 3-butyl-4-hydroxy toluene.

20. The composition of claim 1 further comprising a pigment or dye present in an amount between 0.5% to 5.0% by weight of the composition.

21. The composition of claim 21 wherein the pigment is titanium dioxide or zinc oxide.

22. The composition of claim 1 further comprising an additive selected from the group consisting of solvents, antioxidants, hardeners, plasticizers, opacifiers, colorant extenders, and dispersing agents.

23. A composition capable of polymerizing into a solid form comprising:
    a polymeric filler compound in powder form;
    a polymerization catalyst; and
    acetoxyethyl methacrylate.

24. The composition of claim 23 wherein the polymeric compound is present in an amount between 10% to 90% by weight of the composition.

25. The composition of claim 23 wherein the polymeric compound is an alkyl methacrylate or acrylate polymer.

26. The composition of claim 25 wherein the polymeric compound is selected from the group consisting of poly(methyl methacrylate), poly(ethyl methacrylate), poly(butyl methacrylate), poly(isobutyl methacrylate), poly(ethyl-co-methyl methacrylate), poly(methyl-co-butyl methacrylate), poly(methyl-co-ethyl-co-butyl methacrylate), and poly(ethyl-co-butyl methacrylate).

27. The composition of claim 23 wherein the polymerization catalyst is present in an amount between 0.1% to 5.0% by weight of the composition.

28. The composition of claim 23 wherein the polymerization catalyst is selected from the group consisting of benzoyl peroxide, peroxide, lauroyl peroxide, 5-alkyl barbituric acid, 5-aryl barbituric acid and 1-benzyl-5-phenyl barbituric acid.

29. The composition of claim 23 further including a polymerization promoter present in an amount between 0.1% and 7.0% by weight of the composition.

30. The composition of claim 23 wherein the polymerization promoter is a tertiary aromatic amine.

31. The composition of claim 30 wherein the promoter is selected from the group consisting of N,N-dimethyl-p-toluidine, N,N-diethyl-p-toluidine, N,N-bis(2-hydroxyethyl-p-toluidine, dimethylaminoethyl methacrylate, ethyl-para-dimethylaminoethyl benzoate, and dihydroxyethyl-para-toluidine.

32. The composition of claim 23 further comprising a comonomer or crosslinker present in an amount between 0.1% and 20% by weight of the composition.

33. The composition of claim 32 wherein the comonomer or crosslinker is selected from the group consisting of ethylene glycol dimethacrylate, diethylene glycol dimethacrylate, triethylene glycol dimethacrylate, trimethylolpropane trimethacrylate, 1,4-butanediol dimethacrylate, 1,6-hexanediol dimethacrylate, 1,12-dodecanediol dimethacrylate, polyethylene glycol dimethacrylate, 2,2-bis[4'-(3"-methacryloyl-2"-hydroxypropoxy)phenyl]propane (bis-GMA), ethoxylated bisphenol A dimethacrylate, urethane dimethacrylate, hydroxyethyl methacrylate and hydroxypropyl methacrylate.

34. The composition of claim 23 further comprising a photoinitiator present in an amount between 0.1% to 0.4% by weight of the composition.

35. The composition of claim 34 wherein the photoinitiator is selected from the group consisting of camphorquinone, benzil, 2-hydroxy-2-methyl-1-phenyl-propane-1-one and 1-hydroxycyclohexyl phenyl ketone.

36. The composition of claim 35 further comprising a UV light absorber present in an amount between 0.1% to 3.0% by weight of the composition.

37. The composition of claim 36 wherein the UV light absorber is selected from the group consisting of 2(2'-hydroxy-5'-methyl phenyl)benzotriazole, 2-hydroxy-4-methoxybenzophenone and 2-cyano-3,3'-diphenylacrylic acid 2'-ethylhexyl ester.

38. The composition of claim 23 further comprising a polymerization inhibitor present in an amount between 10 ppm to 5000 ppm.

39. The composition of claim 38 wherein the polymerization inhibitor is a methyl ether of hydroquinone or 3-butyl-4-hydroxy toluene.

40. The composition of claim 23 further comprising a pigment or dye present in an amount between 0.5% to 5.0% by weight of the composition.

41. The composition of claim 40 wherein the pigment is titanium dioxide or zinc oxide.

42. The composition of claim 23 further comprising an additive selected from the group consisting of solvents, antioxidants, hardeners, plasticizers, opacifiers, colorant extenders, and dispersing agents.

* * * * *